(12) United States Patent
Honma et al.

(10) Patent No.: US 8,927,754 B2
(45) Date of Patent: Jan. 6, 2015

(54) SILAZANE COMPOUNDS HAVING FLUOROALKYL GROUP AND METHOD OF PREPARING THE SAME

(75) Inventors: Takayuki Honma, Joetsu (JP); Ayumu Kiyomori, Joetsu (JP); Tohru Kubota, Joetsu (JP); Daijitsu Harada, Joetsu (JP); Hiroyuki Yamazaki, Joetsu (JP); Masaki Takeuchi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 384 days.

(21) Appl. No.: 13/445,074

(22) Filed: Apr. 12, 2012

(65) Prior Publication Data

US 2012/0264962 A1    Oct. 18, 2012

(30) Foreign Application Priority Data

Apr. 12, 2011    (JP) ................. 2011-087870

(51) Int. Cl.
*C07F 7/12*    (2006.01)
*C07F 7/10*    (2006.01)

(52) U.S. Cl.
CPC ....................... *C07F 7/10* (2013.01)
USPC ....................................................... 556/488

(58) Field of Classification Search
CPC ........................................................ C07F 7/12
USPC ....................................................... 566/488
See application file for complete search history.

(56) References Cited

U.S. PATENT DOCUMENTS 4,585,830 A    4/1986 Sweet
5,004,824 A *  4/1991 Takaoka et al. ............. 556/412

FOREIGN PATENT DOCUMENTS

JP    2-011589 A    1/1990
JP    7-094607 B2   10/1995

OTHER PUBLICATIONS

"3.5 Application as Functional Surface Treatment Agent" Silicon Handbook, edited by Itoh Kunio, Kikkan kogyo Shimbun, Ltd., p. 79, Line 9 to p. 80, Line 5, Published on Aug. 31, 1990.(w/partial English translation).

* cited by examiner

*Primary Examiner* — Sudhakar Katakam
*Assistant Examiner* — Kofi Adzamli
(74) *Attorney, Agent, or Firm* — Westerman, Hattori, Daniels & Adrian, LLP

(57) ABSTRACT

Disclosed are silazane compounds having two fluoroalkyl groups, represented by the following general formula (1):

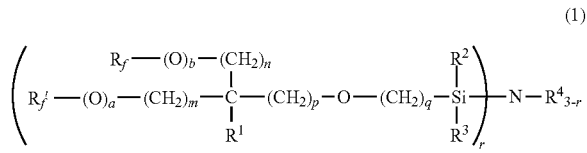

(1)

wherein $R_f$ and $R_f'$ are each a fluoroalkyl group, $R^1$ is a hydrogen atoms or an aliphatic monovalent hydrocarbon group, $R^2$ and $R^3$ are each an aliphatic monovalent hydrocarbon group, $R^4$ is a hydrogen atom or an aliphatic monovalent hydrocarbon group, a and b are each 0 or 1, m, n and p are each an integer of 0 to 6, q is an integer of 1 to 6, and r is 1 or 2. By treating an inorganic material with the silazane compound having two fluoroalkyl groups, high water and oil repellency and high sliding properties can be imparted to the inorganic material in good balance.

5 Claims, 2 Drawing Sheets

SILAZANE COMPOUNDS HAVING FLUOROALKYL GROUP AND METHOD OF PREPARING THE SAME

CROSS-REFERENCE TO RELATED APPLICATION

This non-provisional application claims priority under 35 U.S.C. §119(a) on Patent Application No. 2011-087870 filed in Japan on Apr. 12, 2011, the entire contents of which are hereby incorporated by reference.

TECHNICAL FIELD

The present invention relates to silazane compounds having fluoroalkyl groups which are useful as a surface treating agent, a coating additive, a polymer modifier and the like, and a method of preparing the silazane compounds.

BACKGROUND ART

Hitherto, such organic silicon compounds as alkylalkoxysilane compounds and fluoroalkylalkoxysilane compounds have been known to be useful as surface treating agents, fiber treating agents, coating additives and the like. Especially, it has been known that when a fluoroalkylalkoxysilane compound is used to treat a surface of an inorganic material (for example, glass, metal, or oxide) for the purpose of controlling water repellency, oil repellency or sliding properties (slidability of droplets) of the surface, covalent bonds formed between the silyl group and the surface hydroxyl group of the inorganic material enable strong bonding between the fluoroalkylalkoxysilane compound and the inorganic material, whereby the weather resistance and retention of the modified surface properties are improved ("Silicone Handbook," Edited by Itoh Kunio, Nikkan Kogyo Shimbun, Ltd., p. 79, line 9 to p. 80, line 5).

Alkoxysilane compounds are low in reactivity with the surface hydroxyl group of an inorganic material and, for improving this point, fluoroalkylsilazane compounds having a silazane structure have been developed (JP-B H07-094607).

Where a fluoroalkylalkoxysilane compound or a fluoroalkylsilazane compound is used for surface treatment, such a compound is very effective in improving the static contact angle representing water repellency and oil repellency. In this case, however, the angle at which a droplet starts sliding along the surface treated (sliding angle) as well as the hysteresis ($\theta_A-\theta_R$) obtained from the advancing contact angle ($\theta_A$) and receding contact angle ($\theta_R$) are high; in other words, the improvement in dynamic contact angle is insufficient. The dynamic behavior is particularly important as an index to sliding properties (droplet removal performance), and an improvement thereof is being requested.

In addition, as a compound which can impart water repellency and oil repellency to inorganic materials and which has high reactivity, there have been developed silazane compounds having a perfluoropolyether group (JP-A H02-011589). The silazane compounds, however, have been unsatisfactory in balance between the water and oil repellency and the sliding properties.

SUMMARY OF THE INVENTION

The present invention has been made in consideration of the above-mentioned circumstances. Accordingly, it is an object of the present invention to provide a compound having two fluoroalkyl groups which is high in reactivity with inorganic materials and which, when used to treat an inorganic material, is capable of imparting water and oil repellency and sliding properties to the inorganic material in good balance, and a method of preparing the compound.

In order to attain the above object, the present inventors made extensive and intensive investigations, and, as a result, they found the following. Silazane compounds having a fluoroalkyl group represented by the following general formula (1):

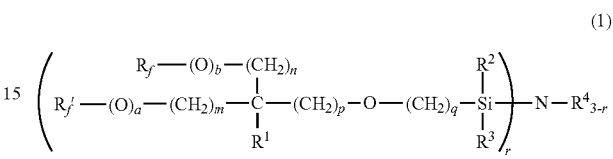

(wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all of hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, a and b are each 0 or 1, m, n and p are each an integer of 0 to 6, q is an integer of 1 to 6, and r is 1 or 2) were found to be high in reactivity owing to the presence of a silazane structure as a hydrolysable group. The silazane compounds having an ether linkage and the two fluoroalkyl groups can impart high water and oil repellency and high sliding properties to inorganic materials in good balance. In addition, the silazane compounds can be easily purified through enhancing volatility by a branched structure. Furthermore, the silazane structure as a hydrolysable group makes it possible to treat an inorganic material with high reactivity, without generating hydrogen chloride. Based on the findings, the present invention has been completed.

According to the present invention, there are provided silazane compounds having fluoroalkyl groups and a method of preparing the silazane compounds, as follows.

[1] A silazane compound having two fluoroalkyl groups and represented by the following general formula (1):

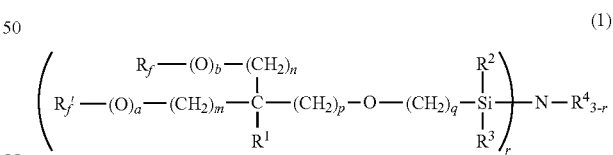

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all the hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, a and b are each 0 or 1, m, n and p are each an integer of 0 to 6, q is an integer of 1 to 6, and r is 1 or 2.

[2] The silazane compound having two fluoroalkyl groups according to the above paragraph [1] which is represented by the following general formula (2):

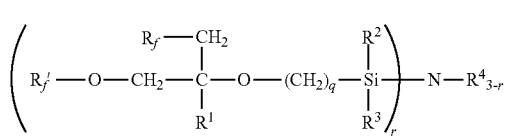

(2)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all the hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, q is an integer of 1 to 6, and r is 1 or 2.

The paragraph [2] is the case where a=1, b=0, m=1, n=1, and p=1 in the formula (1) of the paragraph [1], respectively.

[3] The silazane compound having two fluoroalkyl groups according to the above paragraph [1] which is represented by the following general formula (3):

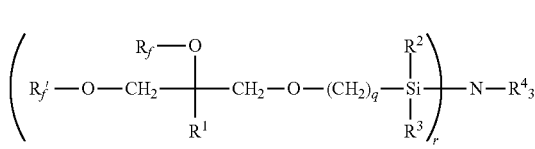

(3)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all of hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, q is an integer of 1 to 6, and r is 1 or 2.

The paragraph [3] is the case where a=1, b=1, m=1, n=0, and p=1 in the formula (1) of the paragraph [1], respectively.

[4] The silazane compound having two fluoroalkyl groups according to the above paragraph [1] which is represented by the following general formula (4):

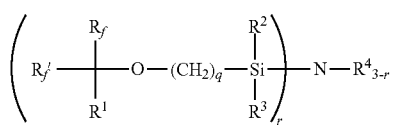

(4)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all the hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, q is an integer of 1 to 6, and r is 1 or 2.

The paragraph [4] is the case where a=0, b=0, m=0, n=0, and p=0 in the formula (1) of the paragraph [1], respectively.

[5] A method of preparing the silazane compound having two fluoroalkyl groups according to any one of the above paragraphs [1] to [4], including reacting a monochlorosilane compound having two fluoroalkyl groups represented by the following general formula (5):

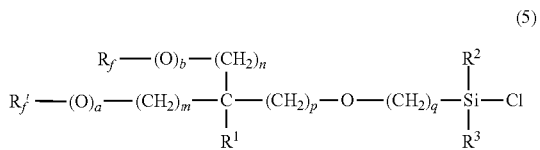

(5)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all of hydrogen atoms bonded to a carbon atom may be substituted, a and b are each 0 or 1, m, n and p are each an integer of 0 to 6, and q is an integer of 1 to 6 with an amine compound represented by the following general formula (6):

$$H_r\text{—}N\text{—}R_{3-r}^4 \qquad (6)$$

wherein $R^4$ is a hydrogen atom or an aliphatic monovalent hydrocarbon group of 1 to 6 carbon atoms, in which part or all of hydrogen atoms bonded to a carbon atom may be substituted, and r is 1 or 2.

ADVANTAGEOUS EFFECTS OF THE INVENTION

According to the present invention, by using the above-mentioned silazane compound having two fluoroalkyl groups to treat an inorganic material, it is possible to impart high water and oil repellency and high sliding properties to the inorganic material in good balance. In addition, the silazane compounds according to the present invention are high in reactivity owing to the presence of the silazane structure and show enhanced volatility owing to the branched structure.

DESCRIPTION OF THE PREFERRED EMBODIMENTS

Figure 1:
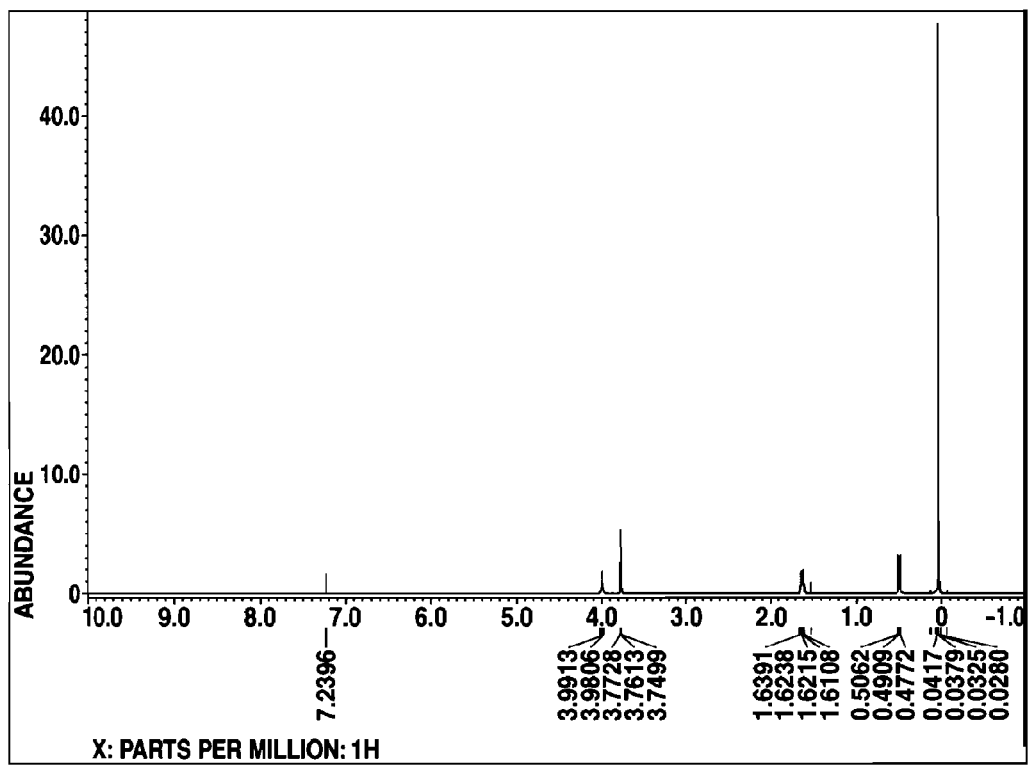
FIG. 1 shows $^1$H-NMR spectrum of a silazane compound obtained in Example 1.

The silazane compound having two fluoroalkyl groups according to the present invention is represented by the following general formula (1):

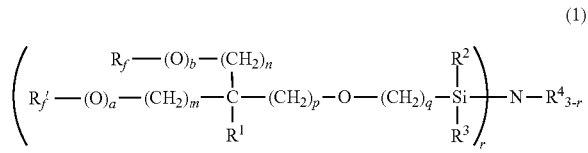

(1)

wherein $R_f$ and $R_f'$ are each a fluoroalkyl group of 1 to 10 carbon atoms, which may respectively be identical or different, $R^1$ is a hydrogen atom or an aliphatic monovalent hydrocarbon group of 1 to 6 carbon atoms, $R^2$ and $R^3$ are each an aliphatic monovalent hydrocarbon group of 1 to 6 carbon atoms, in which part or all the hydrogen atoms bonded to a carbon atom may be substituted and which may respectively be identical or different, $R^4$ is a hydrogen atom or an aliphatic monovalent hydrocarbon group of 1 to 6 carbon atoms, in which part or all of hydrogen atoms bonded to a carbon atom may be substituted, a and b are each 0 or 1, m, n and p are each an integer of 0 to 6, q is an integer of 1 to 6, and r is 1 or 2.

In the general formula (1), $R_f$ and $R_f'$ are each a fluoroalkyl group of 1 to 10 carbon atoms, which may respectively be identical or different. Specific examples of the fluoroalkyl groups include straight chain fluoroalkyl groups such as trifluromethyl, pentafluoroethyl, nonafluorobutyl, tridecafluorohexyl, hexadecafluorooctyl, 2,2,2-trifluroethyl, 3,3,3,2,2-pentafluoropropyl, 5,5,5,4,4,3,3,2,2-nonafluoropentyl, 7,7,7,6,6,5,5,4,4,3,3,2,2-tridecafluoroheptyl, 9,9,9,8,8,7,7,6,6,5,5,4,4,3,3,2,2-hexadecafluorononyl, 3,3,3-trifluropropyl, 4,4,4,3,3-pentafluorobutyl, 6,6,6,5,5,4,4,3,3-nonafluorohexyl, 8,8,8,7,7,6,6,5,5,4,4,3,3-tridecafluorooctyl, 10,10,10,9,9,8,8,7,7,6,6,5,5,4,4,3,3-hexadecafluorodecyl, 4,4,4-trifluorobutyl, 5,5,5,4,4-pentafluoropentyl, 7,7,7,6,6,5,5,4,4-nonafluoroheptyl, 9,9,9,8,8,7,7,6,6,5,5,4,4-tridecafluorononyl, 5,5,5-trifluoropentyl, 6,6,6,5,5-pentafluorohexyl, 8,8,8,7,7,6,6,5,5-nonafluorooctyl, 10,10,10,9,9,8,8,7,7,6,6,5,5-tridecafluorodecyl, 6,6,6-trifluorohexyl, 7,7,7,6,6-pentafluoroheptyl, 9,9,9,8,8,7,7,6,6-nonafluorononyl, 7,7,7-trifluoroheptyl, 8,8,8,7,7-pentafluorooctyl, 10,10,10,9,9,8,8,7,7-nonafluorodecyl, 9,9,9-trifluorononyl, and 10,10,10,9,9-pentafluorodecyl, and branched fluoroalkyl groups such as 1,1,1,3,3,3-hexafluoroisopropyl, and 2,2-bis(trifluoromethyl)propyl.

In the general formula (1), $R^1$ is a hydrogen atom or an aliphatic monovalent hydrocarbon group of 1 to 6 carbon atoms. The aliphatic monovalent hydrocarbon group of 1 to 6 carbon atoms may be a straight chain, branched or cyclic alkyl group, alkenyl group or the like. Specific examples of the aliphatic monovalent hydrocarbon group of 1 to 6 carbon atoms include methyl, ethyl, propyl, isopropyl, butyl, isobutyl, tert-butyl, pentyl, cyclopentyl, hexyl, cyclohexyl, vinyl, allyl, methallyl, and butenyl groups. Preferred examples of $R^1$ are hydrogen atom and methyl group.

In the general formula (1), $R^2$ and $R^3$ are identical or different and each an aliphatic monovalent hydrocarbon group of 1 to 6 carbon atoms, in which part of all of hydrogen atoms bonded to a carbon atom may be substituted, and which may each be a straight chain, branched or cyclic alkyl group, alkenyl group or the like. Specific examples of the groups $R^2$ and $R^3$ include methyl, ethyl, propyl, isopropyl, butyl, isobutyl, tert-butyl, pentyl, cyclopentyl, hexyl, cyclohexyl, vinyl, allyl, methallyl, and butenyl groups, of which preferred are methyl, ethyl, and isopropyl groups. In these groups, at least one of hydrogen atoms bonded to carbon atoms may be substituted. In this case, specific examples of the substituent groups include alkoxy groups such as methoxy, ethoxy, and (iso)propoxy groups; halogen atoms such as fluorine atom, chlorine atom, bromine atom, and iodine atom; cyano group; amino group; aryl groups of 6 to 18 carbon atoms such as phenyl, and tolyl groups; aralkyl groups of 7 to 18 carbon atoms such as benzyl, and phenethyl groups; ester groups; ether groups; acyl groups; sulfide group; alkylsilyl groups; and alkoxysilyl groups.

In the general formula (1), $R^4$ is a hydrogen atom or an aliphatic monovalent hydrocarbon group of 1 to 6 carbon atoms. The aliphatic monovalent hydrocarbon group may be a straight chain, branched or cyclic alkyl group, alkenyl group or the like. Specific examples of the group $R^4$ include a hydrogen atom, methyl, ethyl, propyl, isopropyl, butyl, isobutyl, tert-butyl, pentyl, cyclopentyl, hexyl, cyclohexyl, vinyl, allyl, methallyl, and butenyl groups, of which preferred are methyl, ethyl, and isopropyl groups. In the aliphatic monovalent hydrocarbon group, at least one of hydrogen atoms bonded to carbon atoms may be substituted. In this case, specific examples of the substituent groups include alkoxy groups such as methoxy, ethoxy, and (iso)propoxy groups; halogen atoms such as fluorine atom, chlorine atom, bromine atom, and iodine atom; cyano group; amino group; aryl groups of 6 to 18 carbon atoms such as phenyl, and tolyl groups; aralkyl groups of 7 to 18 carbon atoms such as benzyl, and phenethyl groups; ester group; ether group; acyl groups; sulfide group; alkylsilyl groups; and alkoxysilyl groups.

The letters m, n and p are each an integer of 0 to 6, q is an integer of 1 to 6, and r is 1 or 2. Preferably, m, n and p are each 0 or 1, q is an integer of 1 to 3, and r is 1 or 2.

Specific examples of the compounds represented by the general formula (1) according to the present invention include compounds represented by the following general formula (2) such as Compound A, compounds represented by the following general formula (3) such as Compound B, and compounds represented by the following general formula (4) such as Compound C, but these examples are not restrictive of the present invention.

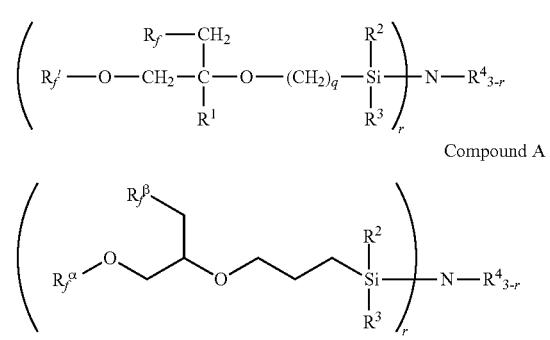

wherein $R_f$ and $R_f'$ are identical or different and each a fluoroalkyl group of 1 to 10 carbon atoms, $R^1$ is a hydrogen atom or an aliphatic monovalent hydrocarbon group of 1 to 6 carbon atoms, $R^2$ and $R^3$ are identical or different and each an aliphatic monovalent hydrocarbon group of 1 to 6 carbon atoms, in which part or all of hydrogen atoms bonded to a carbon atom may be substituted, $R^4$ is a hydrogen atom or an aliphatic monovalent hydrocarbon group of 1 to 6 carbon atoms, in which part of all of hydrogen atoms bonded to a carbon atom may be substituted, q is an integer of 1 to 6, and r is 1 or 2.

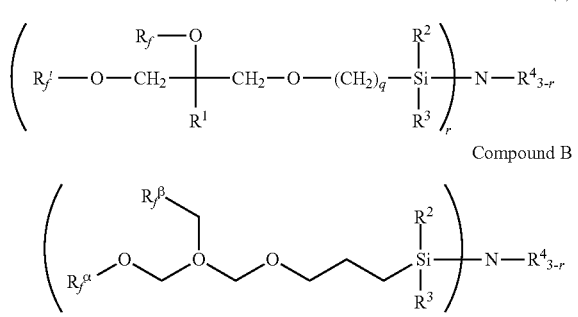

Compound B wherein $R_f$ and $R_f'$ are identical or different and each a fluoroalkyl group of 1 to 10 carbon atoms, $R^1$ is a hydrogen atom or an aliphatic monovalent hydrocarbon group of 1 to 6 carbon atoms, $R^2$ and $R^3$ are identical or different and each an aliphatic monovalent hydrocarbon group of 1 to 6 carbon atoms, in which part or all of hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, q is an integer of 1 to 6, and r is 1 or 2.

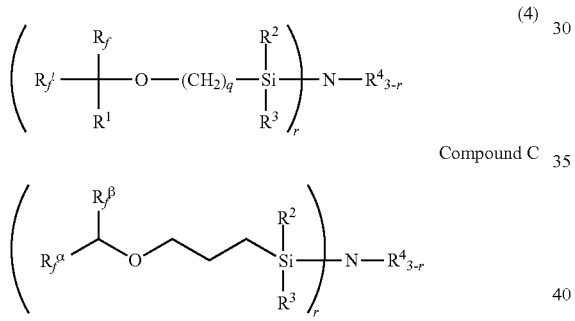

Compound C wherein $R_f$ and $R_f'$ are identical or different and each a fluoroalkyl group of 1 to 10 carbon atoms, $R^1$ is a hydrogen atom or an aliphatic monovalent hydrocarbon group of 1 to 6 carbon atoms, $R^2$ and $R^3$ are identical or different and each an aliphatic monovalent hydrocarbon group of 1 to 6 carbon atoms, in which part or all of hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, q is an integer of 1 to 6, and r is 1 or 2.

Here, examples of $R_f^\alpha$ and $R_f^\beta$ in the compounds A to C include the groups as set forth in the following Table 1, and $R_f^\alpha$ and $R_f^\beta$ may be identical or different.

TABLE 1

| Examples of $R_f^\alpha$ and $R_f^\beta$ in Compounds A to C |
|---|
| —CF$_3$ |
| —(CF$_2$)$_2$F |
| —(CF$_2$)$_4$F |
| —(CF$_2$)$_6$F |
| —(CF$_2$)$_8$F |
| —CH$_2$CF$_3$ |
| —CH$_2$(CF$_2$)$_2$F |

TABLE 1-continued

| Examples of $R_f^\alpha$ and $R_f^\beta$ in Compounds A to C |
|---|
| —CH$_2$(CF$_2$)$_4$F |
| —CH$_2$(CF$_2$)$_6$F |
| —CH$_2$(CF$_2$)$_8$F |
| —(CH$_2$)$_2$CF$_3$ |
| —(CH$_2$)$_2$(CF$_2$)$_2$F |
| —(CH$_2$)$_2$(CF$_2$)$_4$F |
| —(CH$_2$)$_2$(CF$_2$)$_6$F |
| —(CH$_2$)$_2$(CF$_2$)$_8$F |
| —(CH$_2$)$_3$CF$_3$ |
| —(CH$_2$)$_3$(CF$_2$)$_2$F |
| —(CH$_2$)$_3$(CF$_2$)$_4$F |
| —(CH$_2$)$_3$(CF$_2$)$_6$F |
| —(CH$_2$)$_4$CF$_3$ |
| —(CH$_2$)$_4$(CF$_2$)$_2$F |
| —(CH$_2$)$_4$(CF$_2$)$_4$F |
| —(CH$_2$)$_4$(CF$_2$)$_6$F |
| —(CH$_2$)$_5$CF$_3$ |
| —(CH$_2$)$_5$(CF$_2$)$_2$F |
| —(CH$_2$)$_5$(CF$_2$)$_4$F |
| —(CH$_2$)$_6$CF$_3$ |
| —(CH$_2$)$_6$(CF$_2$)$_2$F |
| —(CH$_2$)$_6$(CF$_2$)$_4$F |
| —(CH$_2$)$_8$CF$_3$ |
| —(CH$_2$)$_8$(CF$_2$)$_2$F |
| —CH(CF$_3$)$_2$ |
| —CH$_2$C(CH$_3$)(CF$_3$)$_2$ |

The silazane compound having two fluoroalkyl groups represented by the above general formula (1) may be prepared, for example, by reacting a monochlorosilane compound having two fluoroalkyl groups represented by the following general formula (5):

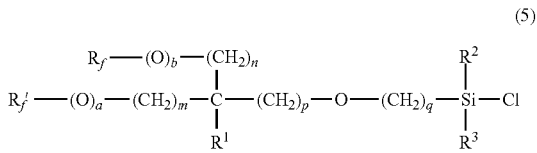

wherein $R_f$ and $R_f'$ are identical or different and each a fluoroalkyl group of 1 to 10 carbon atoms, $R^4$ is a hydrogen atom or an aliphatic monovalent hydrocarbon group of 1 to 6 carbon atoms, $R^2$ and $R^3$ are identical or different and each an aliphatic monovalent hydrocarbon group of 1 to 6 carbon atoms, in which part or all the hydrogen atoms bonded to a carbon atom may be substituted, a and b are each 0 or 1, m, n and p are each an integer of 0 to 6, and q is an integer of 1 to 6 with an amine compound represented by the following general formula (6):

$$H_r\text{—}N\text{—}R_{3-r}^4 \qquad (6)$$

wherein $R^4$ is a hydrogen atom or an aliphatic monovalent hydrocarbon group of 1 to 6 carbon atoms, in which part or all of hydrogen atoms bonded to a carbon atom may be substituted, and r is 1 or 2.

The letters $R_f$, $R_f'$, $R^1$, $R^2$, $R^3$, $R^4$, m, n, p, q, r, a and b in the above general formulas (5) and (6) are the same as defined in the above general formula (1).

Specific examples of the compound represented by the above general formula (5) include the following compounds a to c, which are not restrictive of the present invention.

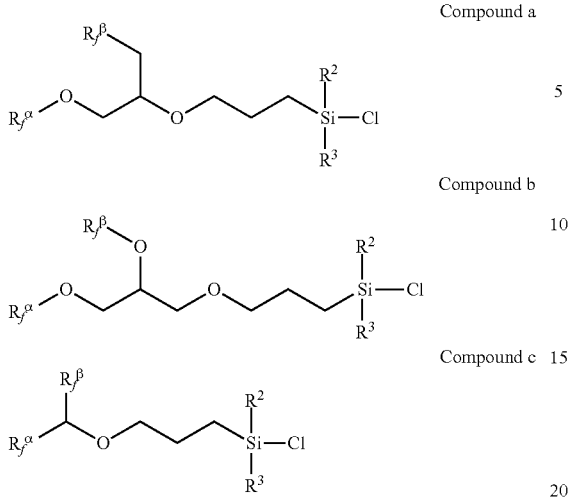

Compound a

Compound b

Compound c

Here, examples of $R_f^\alpha$ and $R_f^\beta$ in the compounds a to c include the groups as set forth in the above Table 1, and $R_f^\alpha$ and $R_f^\beta$ may be identical or different.

Specific examples of the amine compound represented by the general formula (6) used in the above-mentioned reaction include ammonia, methylamine, ethylamine, propylamine, butylamine, dimethylamine, diethylamine, dipropylamine, and dibutylamine, of which preferred are ammonia, methylamine, ethylamine, dimethylamine, and diethylamine.

The ratio between the amount of the monochlorosilane compound of the general formula (5) and the amount of the amine compound of the general formula (6) which are put to the above-mentioned reaction is not particularly limited. From the viewpoint of reactivity and productivity, however, the amount of the amine compound of the general formula (6) is preferably in the range of 2 to 10 mol, particularly 2 to 3 mol, per 1 mol of the compound of the general formula (5).

The above-mentioned reaction is a dehydrochlorination reaction, in which hydrochloric acid is preferably trapped as an ammonium salt by the amine compound. As the amine compound, the compounds of the general formula (6) may be used, and known tertiary amine compounds can be used. Examples of the tertiary amine compounds include triethylamine, amidines such as 1,8-diazabicyclo[5.4.0]-undecene, and nitrogen-containing aromatic compounds such as pyridine, quinoline, isoquinoline, picoline, and lutidine. The amount of the amine compound used is preferably 1.0 to 2.0 mol per 1 mol of the monochlorosilane. The ammonium salt thus produced can be removed by a known method, for example, filtration, liquid separation, or decantation.

In the reaction, a phase-transfer catalyst can be used as a catalyst. Examples of the phase-transfer catalyst include quaternary ammonium halide compounds, quaternary phosphonium halide compounds, and crown ethers. Specific examples include tetramethylammonium chloride, tetraethylammonium chloride, tetrapropylammonium chloride, tetrabutylammonium chloride, trioctylmethylammonium chloride, cetyltrimethylammonium chloride, benzyltrimethylammonium chloride, tetrabutylphosphonium, tetraphenylphosphonium chloride, tetramethylammonium bromide, tetraethylammonium bromide, tetrapropylammonium bromide, tetrabutylammonium bromide, trioctylmethylammonium bromide, cetyltrimethylammonium bromide, benzyltrimethylammonium bromide, tetrabutylphosphonium bromide, tetraphenylphosphonium bromide, tetramethylammonium iodide, tetraethylammonium iodide, tetrapropylammonium iodide, tetrabutylammonium iodide, trioctylmethylammonium iodide, cetyltrimethylammonium iodide, benzyltrimethylammonium iodide, tetrabutylphosphonium iodide, and tetraphenylphosphonium iodide.

The amount of the phase-transfer catalyst to be used is a catalytic amount, which is not particularly limited. From the viewpoint of reactivity and productivity, however, the amount of the phase-transfer catalyst is preferably 0.001 to 1 mol, particularly 0.003 to 0.05 mol, per 1 mol of the monochlorosilane compound of the above general formula (5). If the amount of the catalyst is less than 0.001 mol, a sufficient effect of the catalyst may fail to be exhibited. If the amount of the catalyst exceeds 0.1 mol, on the other hand, it may be impossible to obtain a reaction-accelerating effect corresponding to the catalyst amount.

While the above-mentioned reaction proceeds in a solventless condition, a solvent may be used in the reaction. Examples of the solvent which can be used include hydrocarbon solvents such as pentane, hexane, cyclohexane, heptane, isooctane, benzene, toluene, and xylene; ether solvents such as diethyl ether, tetrahydrofuran, and dioxane; ester solvents such as ethyl acetate, and butyl acetate; aprotic polar solvents such as acetonitrile, and N,N-dimethylformamide; and chlorinated hydrocarbon solvents such as dichloromethane, and chloroform. These solvents may be used either singly or as a mixture of two or more of them. The amount of the solvent to be used is in an ordinary range.

The reaction temperature of the above reaction is not particularly limited, although the reaction temperature is preferably 0 to 120° C., more particularly 0 to 70° C. The reaction time is preferably 1 to 20 hours, more preferably 1 to 10 hours.

Incidentally, olefins as starting material for the compounds a to c can be prepared, for example, by commonly known methods as represented by the following formulas; thus, the compounds a to c can be obtained by reacting the olefin with the corresponding dialkylchlorosilane hydride compound.

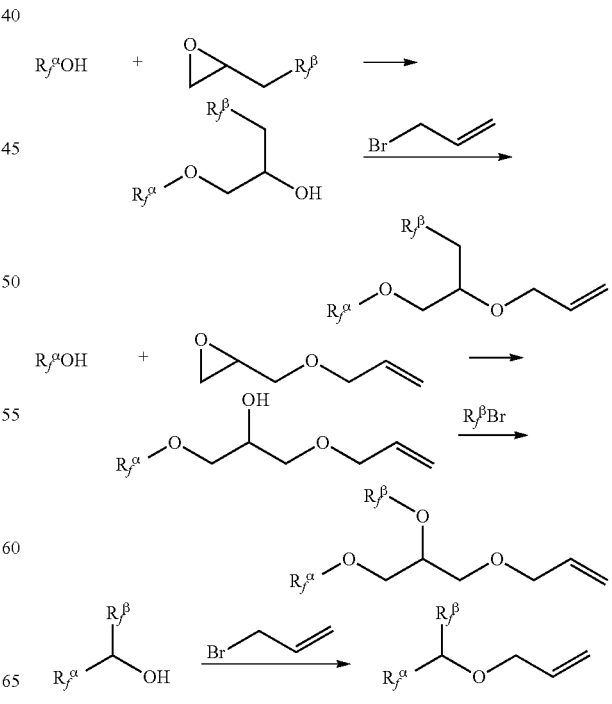

In addition, the compound represented by the general formula (1) can be isolated from the above-mentioned reaction mixture by a purification method such as distillation and column separation; especially, isolation by distillation is preferred, since the compound can be obtained thereby in an enhanced purity. The conditions for distillation are not particularly limited, but it is preferable to carry out the distillation at a reduced pressure, for lowering the boiling point of the objective compound.

While the silazane compounds according to the present invention can be used as they are with no problem, the use of the compounds through dilution with solvent is preferred because of ease of use. Examples of the solvent to be used here include alcohol solvents such as methanol, and ethanol; hydrocarbon solvents such as pentane, hexane, cyclohexane, heptane, isooctane, benzene, toluene, and xylene; ketone solvents such as acetone, and methyl isobutyl ketone; ether solvents such as diethyl ether, tetrahydrofuran, and dioxane; ester solvents such as ethyl acetate, and butyl acetate; aprotic polar solvents such as acetonitrile, and N,N-dimethylformamide; and chlorinated hydrocarbon solvents such as dichloromethane, and chloroform. The concentration of the silazane compound in use through dilution is preferably 0.001 to 50% by weight.

The silazane compounds according to the present invention can be admixed with one or more additives selected from among pigment, anti-foaming agent, lubricant, preservative, pH controlling agent, film forming agent, antistatic agent, anti-fungus agent, surfactant, dye, and the like, within such ranges as not to spoil the effect of the invention.

The use of the silazane compounds according to the present invention is not specifically restricted. Examples of the use of the silazane compounds include an inorganic material surface treating agent, a liquid sealing agent, a casting mold, a resin surface modifier, and a polymer modifier.

By the use of the silazane compounds according to the present invention, a surface treatment (surface modification) of inorganic materials can be performed. Examples of the inorganic materials include metallic plates, glass plates, metallic fibers, glass fibers, powdery silica, powdery alumina, powdery talc, and powdery calcium carbonate. The material of the glass may be a commonly used type of glass, such as E glass, C glass, and silica glass. Silica glass can be used also as a mold material in nanoimprint technology. The glass fibers are not specifically restricted in product form. There are a diversity of glass fiber products, for example, fiber bundles, twines, and woven fabrics formed from glass filaments having a fiber diameter of 3 to 30 μm.

As the method for treating an inorganic material by the use of the silazane compound, the conventional methods can be used. The applicable methods include a method in which the inorganic material is immersed in the silazane compound used as it is or in a diluted state, followed by taking out the inorganic material therefrom and drying it, a method in which the silazane compound as it is or in a diluted state is sprayed to the surface of the inorganic material, followed by drying the inorganic material, and a method in which the inorganic material is brought into contact with an inert gas accompanied by the silazane compound.

EXAMPLES

Now, the present invention will be described specifically by showing Synthesis Example, Examples, and Comparative Example, but the invention is not to be restricted by the following Examples.

Synthesis Example 1

A flask equipped with a stirrer, a reflux condenser, a dropping funnel and a thermometer was charged with 268 g (1.3 mol) of an olefin represented by the following formula (7),

(7)

and a toluene solution of a platinum-1,3-divinyl-1,1,3,3-tetramethyldisiloxane complex ($2.0 \times 10^{-4}$ mol based on the olefin), followed by heating to 70° C. After the internal temperature became stable, 123 g (1.3 mol) of dimethylchlorosilane was added dropwise to the flask over five hours at 65 to 75° C., and the reaction mixture was stirred at that temperature for two hours. By distillation, 360 g of a colorless transparent fraction with a boiling point of 96° C./5.0 kPa was obtained, which was confirmed to be a compound of the following formula (8).

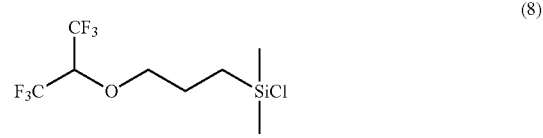

(8)

Example 1

A flask equipped with a stirrer, a reflux condenser, a dropping funnel and a thermometer was charged with 182 g (0.60 mol) of the compound of the above general formula (8) and 300 g of toluene, and ammonia gas was fed thereinto at room temperature over three hours. After the pH of the exhaust gas changed to be basic, a salt was removed by filtration. By distillation of the reaction mixture thus obtained, 140 g of a colorless transparent fraction with a boiling point of 121 to 122° C./0.2 kPa was obtained.

Figure 2:
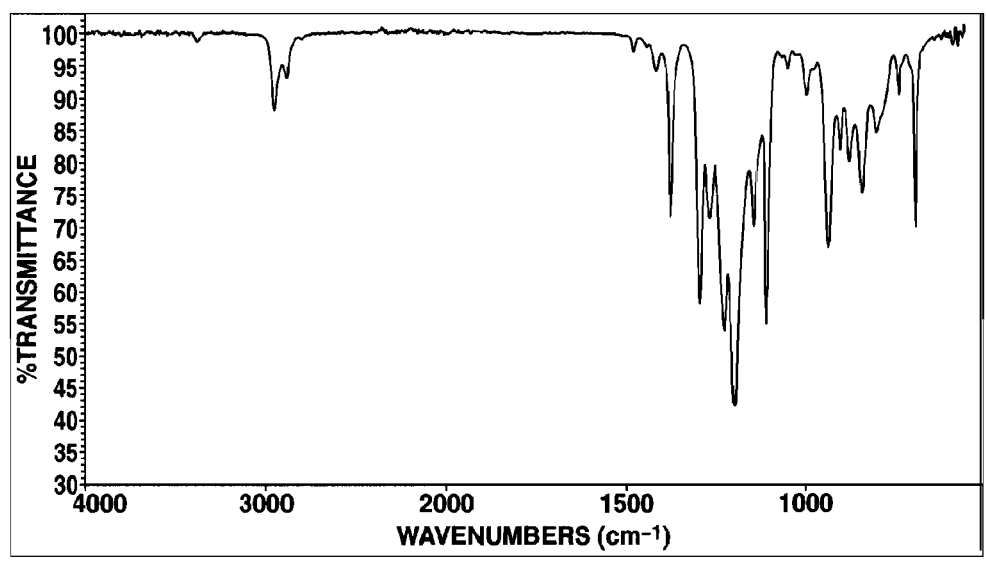
FIG. 2 shows IR spectrum of the silazane compound obtained in Example 1.

The fraction obtained was subjected to measurement of mass spectrum, $^1$H-NMR spectrum (heavy chloroform solvent), and IR spectrum, by a chemical ionization method using isobutane gas as a reaction gas. The result of mass spectrum is set forth below. In addition, FIG. 1 shows a $^1$H-NMR spectrum chart, and FIG. 2 shows an IR spectrum chart.

Mass Spectrum: m/z 550, 398, 267, 202, 142

Based on the above results, the compound obtained was identified as a compound of the following formula (9).

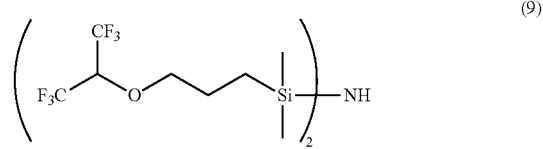

(9)

Example 2

A flask equipped with a stirrer, a reflux condenser, a dropping funnel and a thermometer was charged with 32 g (0.44 mol) of diethylamine and 100 g of toluene. Then, 61 g (0.20 mol) of the compound of the above general formula (8) was added dropwise to the flask over three hours under water cooling, and the mixture in the flask was stirred for three hours at room temperature. After a salt was removed by filtration, the resulting reaction mixture was distilled, to obtain 57 g of a colorless transparent fraction with a boiling point of 97 to 98° C./2.0 kPa.

Figure 3:
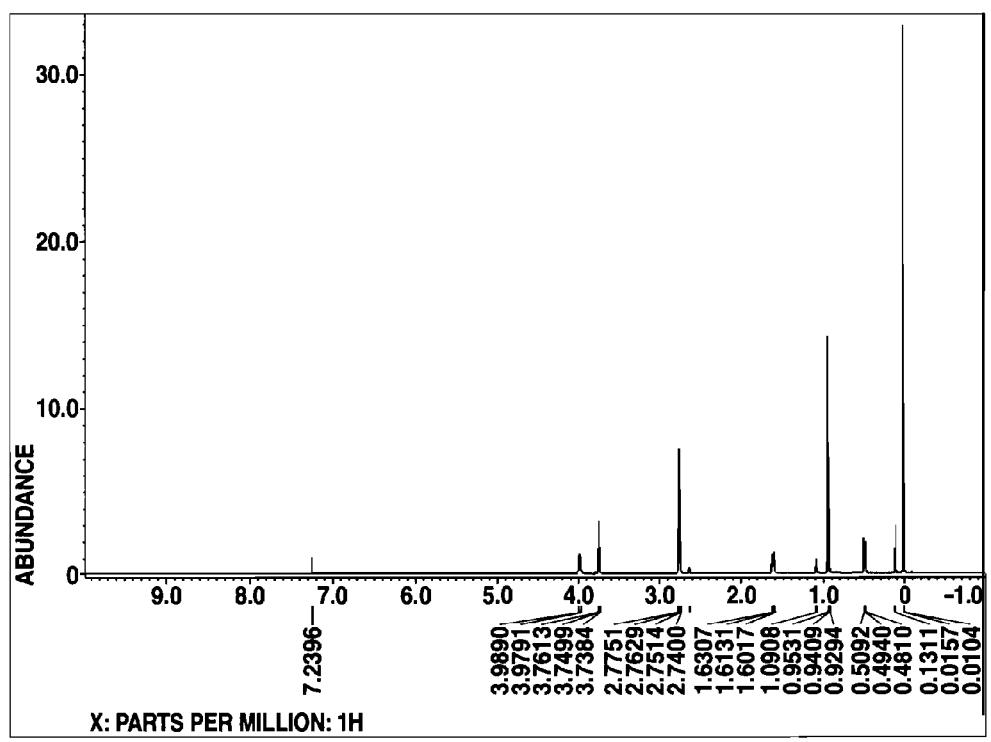
FIG. 3 shows $^1$H-NMR spectrum of a silazane compound obtained in Example 2.
Figure 4:
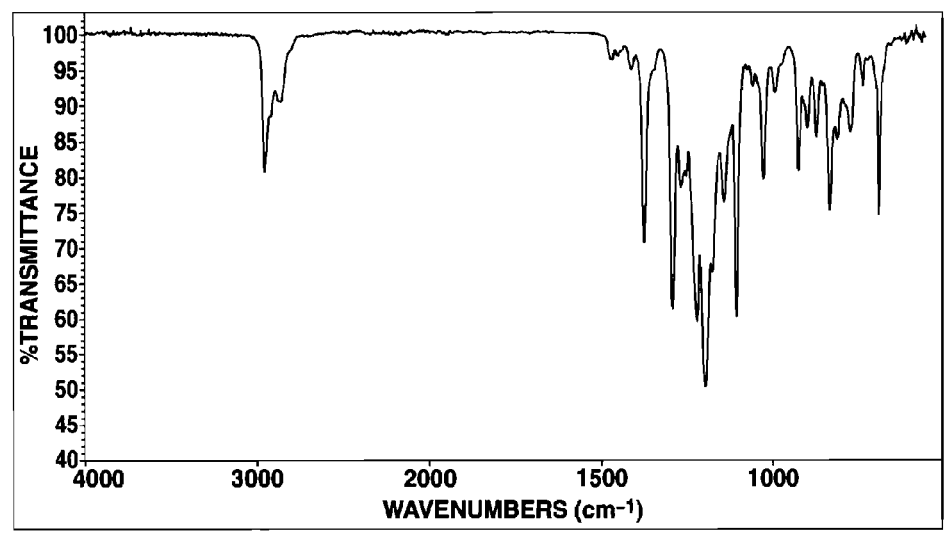
FIG. 4 shows IR spectrum of the silazane compound obtained in Example 2.

The fraction thus obtained was subjected to measurement of mass spectrum, $^1$H-NMR spectrum (heavy chloroform solvent), and IR spectrum. The result of mass spectrum is set forth below. In addition, FIG. 3 shows a $^1$H-NMR spectrum chart, and FIG. 4 shows an IR spectrum chart.

Mass Spectrum: m/z 339, 324, 267, 225, 130

Based on the above results, the compound obtained was identified as a compound of the following formula (10).

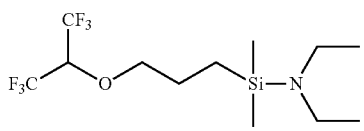

(10)

Examples 3, 4 and Comparative Example 1

Use as Glass Surface Treating Agent

A glass plate made to be hydrophilic by a UV ozone treatment was immersed in each of the silazane compounds having fluoroalkyl groups synthesized in the above Examples and a commercial fluoroalkylsilazane compound for two hours, followed by ultrasonic cleaning in ethanol and drying at 110° C. for 30 minutes. Onto the glass plate thus surface-treated, water (1 μl) or tetradecane (5 μl) was dropped, and the contact angle was measured. Sliding angle was measured by a method in which water (13 μl) was dropped onto a glass plate, then the glass plate was tilted, and the tilting angle at which the water droplet started moving was measured. In addition, the difference (hysteresis) between the advancing contact angle and the receding contact angle was calculated. The results are shown in Table 2 below.

Incidentally, the fluoroalkylsilazane compound used in Comparative Example 1 is a compound of the following formula (11).

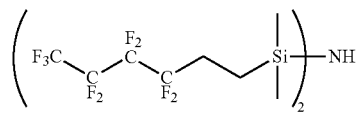

(11)

TABLE 2

|  | Silane compound | Contact angle (°) Water | Contact angle (°) Tetradecane | Sliding angle (°) Water | Hysteresis |
|---|---|---|---|---|---|
| Example 3 | Compound of Example 1 | 95 | 41 | 19 | 14 |
| Example 4 | Compound of Example 2 | 95 | 42 | 18 | 12 |

TABLE 2-continued

|  | Silane compound | Contact angle (°) Water | Contact angle (°) Tetradecane | Sliding angle (°) Water | Hysteresis |
|---|---|---|---|---|---|
| Comparative Example 1 | Compound of Comparative Example 1 | 92 | 41 | 43 | 26 |

From the above measurement results, the silazane compounds according to the present invention were found to have water repellency and oil repellency. The silazane compounds of the invention were also found to have excellent sliding properties, based on the fact that the water droplet thereon starts sliding at a low sliding angle and the hysteresis is small.

Japanese Patent Application No. 2011-087870 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A silazane compound having two fluoroalkyl groups and represented by the following general formula (1):

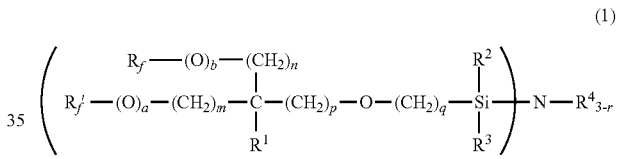

(1)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all the hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, a and b are each 0 or 1, m, n and p are each an integer of 0 to 6, q is an integer of 1 to 6, and r is 1 or 2.

2. The silazane compound having two fluoroalkyl groups according to claim 1 which is represented by the following general formula (2):

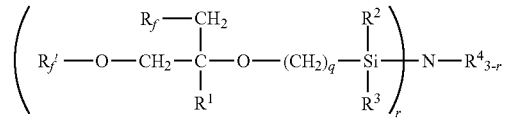

(2)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all the hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, q is an integer of 1 to 6, and r is 1 or 2.

3. The silazane compound having two fluoroalkyl groups according to claim 1 which is represented by the following general formula (3):

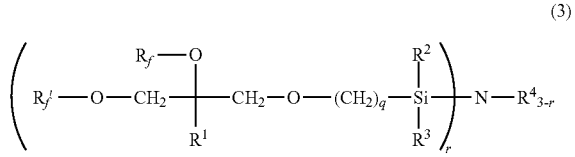

(3)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all of hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, q is an integer of 1 to 6, and r is 1 or 2.

4. The silazane compound having two fluoroalkyl groups according to claim 1 which is represented by the following general formula (4):

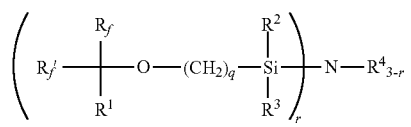

(4)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all the hydrogen atoms bonded to a carbon atom may be substituted, $R^4$ is a hydrogen atom or an aliphatic monovalent hydrocarbon group of 1 to 6 carbon atoms, in which part or all of hydrogen atoms bonded to a carbon atom may be substituted, q is an integer of 1 to 6, and r is 1 or 2.

5. A method of preparing the silazane compound having two fluoroalkyl groups according to any one of claims 1 to 4, comprising
reacting a monochlorosilane compound having two fluoroalkyl groups represented by the following general formula (5):

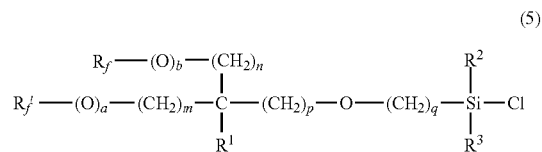

(5)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently an aliphatic monovalent hydrocarbon group of 1 to 6 carbon atoms, in which part or all of hydrogen atoms bonded to a carbon atom may be substituted, a and b are each 0 or 1, m, n and p are each an integer of 0 to 6, and q is an integer of 1 to 6 with an amine compound represented by the following general formula (6) :

(6)

wherein $R^4$ is a hydrogen atom or an aliphatic monovalent hydrocarbon group of 1 to 6 carbon atoms, in which part or all of hydrogen atoms bonded to a carbon atom may be substituted, and r is 1 or 2.

* * * * *